(12) United States Patent
Imamura et al.

(10) Patent No.: US 8,333,712 B2
(45) Date of Patent: Dec. 18, 2012

(54) BODY FLUID SAMPLING DEVICE

(75) Inventors: Takeshi Imamura, Chigasaki (JP);
Norihiko Utsunomiya, Machida (JP);
Naoto Mihashi, Nerima-ku (JP)

(73) Assignee: Canon Kabushiki Kaisha, Tokyo (JP)

( * ) Notice: Subject to any disclaimer, the term of this patent is extended or adjusted under 35 U.S.C. 154(b) by 1228 days.

(21) Appl. No.: 11/617,308

(22) Filed: Dec. 28, 2006

(65) Prior Publication Data
US 2007/0161926 A1 Jul. 12, 2007

(30) Foreign Application Priority Data

Jan. 11, 2006 (JP) ................................. 2006-003658

(51) Int. Cl.
*A61B 5/00* (2006.01)

(52) U.S. Cl. ...................................................... 600/583

(58) Field of Classification Search .................. 600/583, 600/584; 606/181–183
See application file for complete search history.

(56) References Cited

U.S. PATENT DOCUMENTS
2003/0088191 A1 * 5/2003 Freeman et al. .............. 600/583

FOREIGN PATENT DOCUMENTS
JP 2006-239062 A 9/2006

* cited by examiner

*Primary Examiner* — Brian Szmal
(74) *Attorney, Agent, or Firm* — Canon U.S.A., Inc., IP Division

(57) ABSTRACT

A body fluid sampling device comprises an elastic membrane arranged at a part of a hermetically sealed housing having a communication path with a check valve and a needling means arranged beneath the membrane. As the membrane is pressed by a fingertip, the needling means needles through the membrane and further the skin of the fingertip to exude blood. As the fingertip is then separated from the membrane, the exuded blood is efficiently introduced into the housing due to the negative pressure produced in the internal region by the elastic movement of the membrane.

4 Claims, 4 Drawing Sheets

BODY FLUID SAMPLING DEVICE

BACKGROUND OF THE INVENTION

1. Field of the Invention

This invention relates to a body fluid sampling device for analyzing and quantifying the ingredients contained in body fluid such as blood, lymph and intercellular liquid. More specifically, the present invention relates to a body fluid sampling device that is highly advantageous to the subject when the subject samples body fluid by him- or herself because of simplicity and correctness and the low risk of intrusion and admixture of impurities.

2. Description of the Related Art

The importance of health examinations including medical checkups has been increasing in recent years due to the rising tide of the social concern to the health and the increase in the number of patients of lifestyle related diseases that are attributable to changes in the diet and the lifestyle. On the other hand, there is a tendency of trying to grasp the health condition of each individual by him- or herself because of the high cost of medical treatments in our aging society with fewer children. Actually, so-called mail health examination systems of sampling own blood and sending it to a relevant examination facility by mail have already started to operate for biochemical examinations such as liver function tests and immunity examinations for infectious diseases and tumor markers to say nothing of measurement of the blood sugar level.

Furthermore, devices adapted to examine the body fluid sampled by the subject on site have been developed by exploiting microprocessing technologies and micro-fluid control technologies. As for such micro-devices for physical examinations, the techniques relating to body fluid and sampled body fluid specimens as listed below have been disclosed to date.

Japanese Patent Application Laid-Open No. 2002-263085 discloses a method of sampling blood by a small quantity by means of which it is possible to complete the sequence of a blood sampling process simply by pushing a small sampling mechanism against the skin surface of the sampling site typically by a fingertip. Japanese Patent Application Laid-Open No. 2003-083958 discloses a method of sampling blood by enclosing the outer periphery of a syringe by means of a cylinder in order to keep the inside airtight and produce negative pressure there so as to suck in the skin and make it protrude and then driving the syringe needle to needle the skin. The Patent Document describes that the syringe can be positioned and anchored reliably by such a needling method. Japanese Patent Application Laid-Open No. 2000-185034 discloses a blood sampling/analyzing device comprising a very small blood sampling needle formed by molding silicone with a hollow internal section disposed in the needle body, a pump section and an analyzing section arranged on a single substrate.

All the above-listed known blood fluid sampling devices are devised in such a way that the liquid conveying element, the analyzing element and the needling means such as a sampling needle are interlocked so that the sampled body fluid such as blood may not be exposed to the outside and only a small quantity of body fluid is sufficient for the analysis. However, such devices basically require an arrangement for bringing the needling means close to the surface of the skin or the mucous membrane of a living body, needling the skin or the mucous membrane and sucking the body fluid taken out from the body after the needling by means of a special mechanism arranged at the device side. Such an arrangement more often than not makes the device a complex one. Thus, it may be very useful to provide a body fluid sampling device that can meet the following performance requirements.

(1) The psychological barrier against needling is reduced and the subject can positively and autonomously control the pain produced by the needling.

(2) The body fluid taken out from the body by the needling means can be conveyed into the device without using a special sucking means or sucking mechanism.

SUMMARY OF THE INVENTION

An object of the present invention is to provide a body fluid sampling device and a body fluid analyzing device arranged to satisfy the above requirements.

According to the present invention, the above object is achieved by providing a body fluid sampling device for sampling body fluid from a body fluid sampling surface of a living body, the device comprising: a housing having a hermetically sealable internal region; a pressurizing section arranged at a part of a partition wall separating the internal region from an outside and adapted to be applied to the body fluid sampling surface; needling means arranged in the internal region so as to needle the body fluid sampling surface and cause body fluid to exude to the body fluid sampling surface; and negative pressure generating means for generating negative pressure in the internal region, the needling means being arranged at a position adapted to needle through the pressurizing section when the pressurizing section is pressed by the body fluid sampling surface to produce a through hole in the pressurizing section and further needle through the body fluid sampling surface, the negative pressure generating means having a mechanism for generating negative pressure in the internal region when the body fluid sampling surface is separated from the pressurizing section.

According to the present invention, it is also possible to provide a body fluid analyzing device having a body fluid sampling feature by adding a body fluid analyzing means to a body fluid sampling device according to the invention.

BRIEF DESCRIPTION OF THE DRAWINGS

FIG. 1A is a schematic vertical cross sectional view of the device and FIG. 1B is a schematic plan view thereof;

FIG. 2A is a schematic vertical cross sectional view of the device and FIG. 2B is a schematic plan view thereof;

DETAILED DESCRIPTION OF THE PREFERRED EMBODIMENTS

Figure 1A:
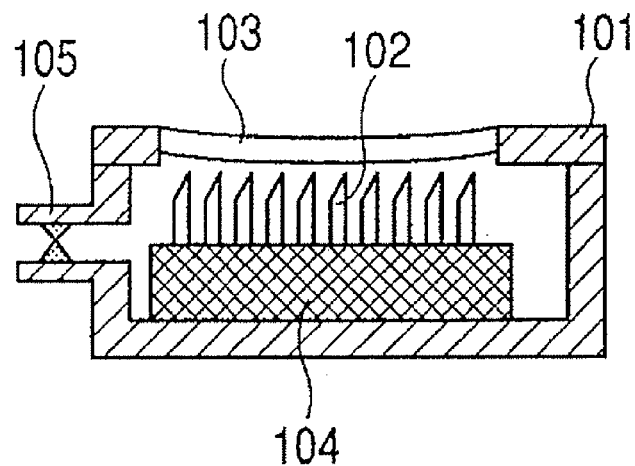
FIGS. 1A and 1B are schematic illustrations of an embodiment of body fluid sampling device according to the invention, showing the configuration thereof.
Figure 1B:
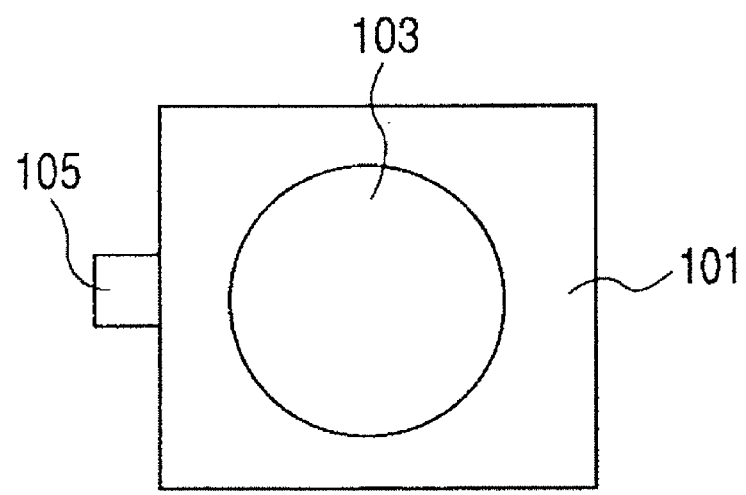

Now, a preferred embodiment of body fluid sampling device according to the present invention will be described by referring to FIGS. 1A and 1B. FIGS. 1A and 1B are schematic illustrations of an embodiment of body fluid sampling device according to the invention, showing the configuration thereof. FIG. 1A is a schematic vertical cross sectional view of the device and FIG. 1B is a schematic plan view thereof. The body fluid sampling device comprises a housing 101 having an internal region and a needling means 102 arranged on a support body 104 vis-à-vis a membrane 103 that constitutes a pressurizing section to be pressed against the part of the body surface of a living body selected as body fluid sampling surface. A check valve 105 is arranged at a part of the housing 101 to allow gas to flow from the inside to the outside of the housing 101 but checks any gas trying to flow into the inside from the outside of the housing 101.

It is sufficient for the needling means 102 to have one or more than one projections whose tips can needle through the body surface. One or more than one needles may typically be used as needling means. When needles are used, stainless steel needles may be most popular, although needles of any other material may alternatively be used so long as they provide a sufficient degree of strength and safety for needling. For example, needles made of silicone or reinforced plastic may suitably be used for the purpose of the present invention. The needling means is required to have a needling capability at the tips thereof that is sufficient for needling the body surface and extracting body fluid such as blood. Preferably, the needling means additionally has a structure that can guide the body fluid exuded to the body surface to the inside of the housing with ease. When needles are used, they preferably have a hollow structure having a through hole therein getting to the support body 104 or provided on the lateral surface thereof with a body fluid guiding structure such as a micro groove that is continuous all the way to the support body 104. The diameter and the length of the needles, the tip structure thereof, the number of needles and the mode of arrangement of needles on the support body may be selected appropriately depending on the type and the size of the selected body surface, which may be a fingertip, and the type of body fluid to be sampled.

The needling means 102 is supported by the support body 104. In the illustrated instance, the support body 104 also has a function of storing the introduced body fluid. Normally, a spongy substance, a porous substance or a filmy substance having strength sufficient for supporting the needling means 102 is used for the support body 104.

The membrane 103 is part of the partition wall that separates the internal region of the housing 101 and the outside and operates as pressurizing section. The membrane 103 is made of an elastic substance. As the membrane 103 is pressed against the body surface typically by means of a fingertip, the membrane 103 is bent by the pressure applied by the body surface to the membrane 103 and exerts repulsive force, trying to restore the condition before being bent. Due to the bend, two actions including an action for producing negative pressure in the internal region of the device and an action for causing the needling means to needle the body surface take place simultaneously. The membrane 103 can be pressed against the body surface by pressing it at least from the side of the device or the side of the body surface.

In the action for producing negative pressure, firstly positive pressure is produced at the side of the internal region of the device as the membrane 103 is bent toward the internal region of the device. As a result, gas (air) is forced out from the internal region to the outside by way of the check valve 105 by the volume that corresponds to the bend toward the internal region of the device. As the membrane 103 is separated from the body surface that is exerting pressure on the membrane 103 under this condition, the pressure being applied to the membrane 103 by the body surface is released and then the membrane 103 tries to restore the original condition due to the elastic repulsive force thereof. At this time, since the check valve 105 allows gas to flow from the internal region to the outside but checks gas trying to flow from the outside into the internal region, negative pressure is produced in the internal region of the housing relative to the outside.

In the action for needling the body surface, the membrane 103 gets to the front end of the needling means 102 and, as pressure is applied further, the needling means 102 needles through the membrane 103 and then needles the body surface. As a result, body fluid such as blood exudes from the body surface.

The exuded body fluid is held between the body surface and the outer surface of the membrane 103. On the other hand, through holes are formed through the membrane 103 as a result of the movement of the front end of the needling means 102 through the membrane 103 when the membrane 103 is pressurized so that the body fluid is guided effectively into the device by way of the through holes due to the produced negative pressure. More specifically, negative pressure is produced in the internal region of the device and, as air flows from the outside into the internal region by way of the through holes formed through the membrane 103 by the needling means 102 to compensate the reduced pressure, the body fluid exuded from the body surface is driven into the inside of the device at the same time.

When needles having a hollow structure are used for the needling means 102, it is possible to efficiently guide body fluid into the device both through the gaps between the lateral surfaces of the needles and the membrane 103 and the hollow sections of the needles. When needles provided with an axially continuously extending micro groove are used, micro channels are formed between the lateral surfaces of the needles and the membrane 103 for body fluid so that it is possible to effectively guide body fluid into the device through the micro channels. Additionally, since the membrane 103 is made of an elastic substance, the body fluid coming out to the contact sections of the membrane 103 and the needling means 102 can be satisfactorily held there and reliably guided into the device.

As described above, as the membrane 103 is pressed, (1) the phenomenon of drawing out air from the inside of the device through the check valve 105 by the volume corresponding to the pressure applied to the membrane 103, and (2) the phenomenon of introducing the body fluid exuded as a result of needling into the device through the micro pores of the membrane 103 formed by the needling means 102 when the pressure is released and the membrane 103 restores the original condition take place instantaneously.

An elastic rubber like material such as silicon rubber can suitably be used for the elastic substance of the membrane 103.

When the support body 104 is made of a porous material such as sponge, the body fluid introduced into the internal region of the device can be collected with ease. Once body fluid is sampled, it can be taken out of the device with the support body 104 and subjected to various examinations as specimen.

Figure 2A:
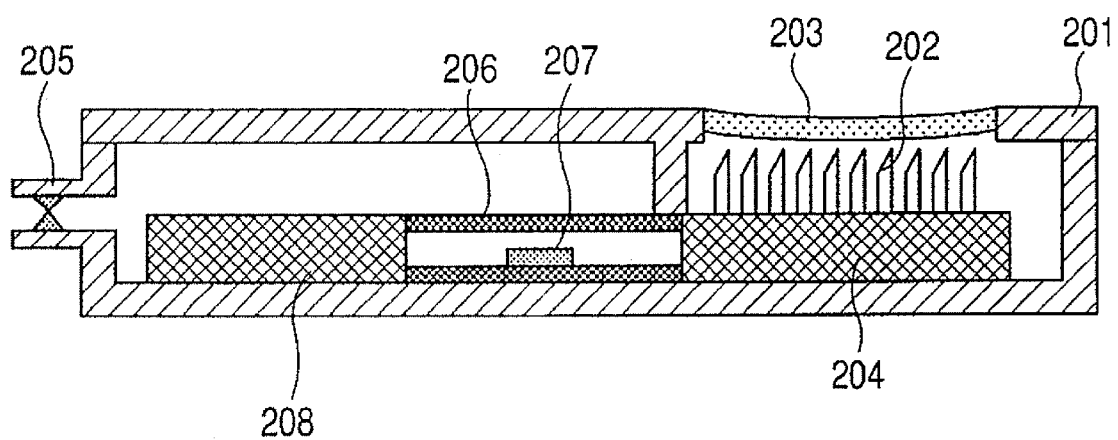
FIGS. 2A and 2B are schematic illustrations of an embodiment of analyzing device having a body fluid sampling feature according to the invention, showing the configuration thereof.
Figure 2B:
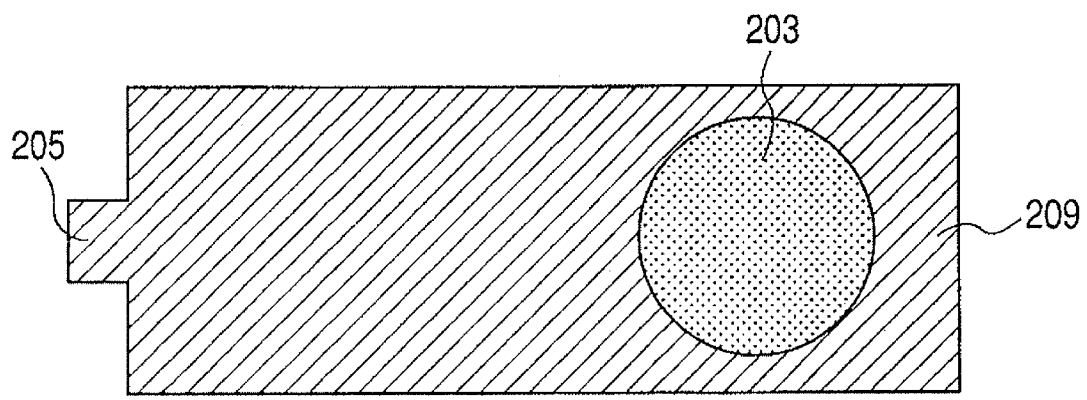

According to the present invention, it is possible to provide a body fluid analyzing device having a body fluid sampling feature by adding a body fluid analyzing means to the inside of a body fluid sampling device according to the invention. FIGS. 2A and 2B schematically illustrate a preferred embodiment of analyzing device according to the invention. FIG. 2A is a schematic vertical cross sectional view of the device and FIG. 2B is a schematic plan view thereof. This device also comprises a housing 201, a needling means 202, a membrane 203, a support body 204 and a check valve 205, which operate in respective manners as described above by referring to FIGS. 1A and 1B. In this device, the support body 204 is provided with a filtering feature of separating blood corpuscles to accommodate a situation where blood is used as body fluid specimen along with strength sufficient for support the needling means 202. Any structure and any material may be used for the support body that is provided with a filtering feature so long as the support body shows micropores of a sub-micron size that allow body fluid to pass but block blood corpuscles. Normally, an inorganic material selected from porous silica materials and glass filters or an organic material selected from cellulose derivatives and polysulfone filters is used for it. The surface of the selected material may be coated with hydrophilic polymer or the like in order to prevent adsorption of the substance of the object of examination in the body fluid extracted as specimen from taking place.

The body fluid that gets to the support body 204 operating as filter and becomes filtered (blood plasma if the body fluid specimen is blood) is then moved into a liquid transport path 206 due to the capillary phenomenon and brought into contact with a reaction/detection section 207. While the reaction/detection section 207 is illustrated as a member independent from the liquid transport path 206 in FIGS. 2A and 2B, a mode of realization where the liquid transport path 206 and the reaction/detection section 207 are integrated such as the one used popularly for immunochromatography is also possible. When the reaction/detection section 207 is formed as a member independent from the liquid transport path 206, the liquid transport path 206 is a micro liquid transport path having a diameter of hundreds of several micrometers to tens of several micrometers. In the case of an arrangement where the liquid transport path 206 and the reaction/detection section 207 are integrated such as the one used popularly for immunochromatography, the liquid transport path 206 is a so-called filter for a test strip (paper filter or polymer film).

The reaction/detection section 207 can be formed in various different ways depending on the object of analysis and a plurality of such sections may be arranged on the liquid transport path 206. For example, when a tumor marker protein (AFP, PSA, CEA or the like) in body fluid is to be analyzed as target, the sandwich immunoassay method may be used. If such is the case, body fluid moves through the liquid transport path 206 to get to the reaction/detection section 207 and a primary antibody-target-secondary antibody complex is formed at the part of the primary antibody fixed onto the reaction/detection section 207 when a labeled secondary antibody is arranged between the support body 204 and the reaction/detection section 207. When the label of the secondary antibody is an enzyme, the device can be used as an enzyme immunoassay (EIA or ELISA) device for applying an enzyme substrate to the enzyme by means of a known technique that is not described here and optically detecting the substrate that is transformed by the enzyme. When the label of the secondary antibody is an enzyme or a catalyst and the product produced as the enzyme substrate or the precursor on which the catalyst acts is transformed by the enzyme or the catalyst, whichever appropriate, is a light emitting product, the device can be used as a chemiluminescence immunoassay (CLIA) device. When a fluorescent material is used as label, the device can be used as fluorescence immunoassay (FIA) device for measuring the fluorescence generated by excitation light produced for a light source (not shown) for the analytical purposes. Furthermore, the device can be used as an electro-chemiluminescence immunoassay (ECLIA) device for using a ruthenium complex such as ruthenium tribipyridine as label and causing it to emit light on an electrode by way of an electrolytic reaction.

The device can also be used as a plasmon resonance device by arranging a thin film or a pattern of a metal such as gold or silver that produces plasmon resonance on the surface of the reaction/detection section 207 and then arranging an analyzing means formed by fixing a captor of the target such as antibody on the thin film or the pattern, whichever appropriate. With such an analysis device utilizing plasmon resonance, it is possible to optically detect the amount or concentration of the target (substance to be detected) by causing the body fluid containing the target to contact the captor on the metal.

When ions such as sodium ions, potassium ions or calcium ions contained in body fluid are the object of analysis, an ion-selective electrode for such ions is arranged in the region 207 of the liquid transport path 206 and the object of analysis is analyzed by detecting the change in the electric signal.

When an organic low molecular weight compound such as glucose or lactic acid contained in body fluid is the object of detection, it is generally possible to use a technique of arranging an enzyme electrode formed by mounting and fixing oxidoreductase such as glucose oxidase, glucose dehydrogenase or lactate dehydrogenase on electrode substrate and analyzing the exchange of electrons on the electrode by way of the electric current value. When the enzyme to be fixed is ALP, γ-GTP or the like, it is possible to use a technique of optically detecting the product produced as a result of transformation of the substrate thereof.

On the other hand, the liquid collecting section 208 is a part for collecting the liquid after the end of the reaction/detection process and may simply be a hollow container with or without a liquid absorbing material. By preparing the liquid transport path 206 as a capillary structure of the above-described dimension, it is possible to transport liquid in the direction toward the liquid collecting section 208. Additionally, when the membrane 203 is pressed to drive air out through the check valve 205 and the membrane 203 restores the original condition, the negative pressure is raised to a slight extent at the left side part because the left part of the housing is partitioned. Then, the liquid can be discharged from the liquid transport path 206 to the liquid collecting section 208 more effectively. Still additionally, the liquid collecting section 208 may be hermetically sealed with a small aperture equipped with a check valve or some other means that can make the internal pressure of the liquid collecting section 208 lower than the internal pressure of the support body 204.

EXAMPLES

Now, the present invention will be described more specifically by way of examples. Note, however, the present invention is by no means limited by the examples.

Example 1

Figure 4:
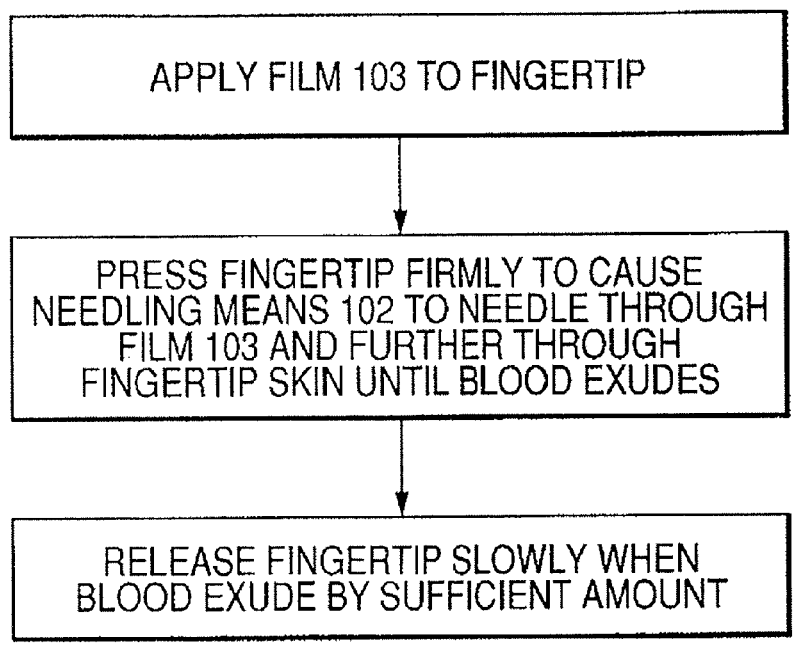
FIG. 4 is a flowchart of the body fluid sampling process of Example 1.

An example of sampling blood by means of a body fluid sampling device according to the invention will be described below by referring to FIGS. 1A and 1B and the flowchart of FIG. 4. Firstly, an index finger or middle finger is applied onto the membrane 103 of the body fluid sampling device as shown in FIG. 1. The bottom of the device may be rigidly secured onto a desk or the like or supported by a thumb. Then, the finger applied onto the membrane 103 is pressed firmly. The extent (displacement) and the time of pressing are such that the needling means (which is needling needles in this case) 102 needles through the membrane 103 and further through the skin of the fingertip to cause a sufficient amount of blood to be exuded so as to achieve the objective of blood sampling.

At this time, air is discharged from the inside of the device to the outside by way of the check valve 105 by a quantity corresponding to the extent of deformation of the membrane 103 produced by the fingertip applied thereto. Once a sufficient amount of blood is sampled, the fingertip pressed against the membrane 103 is released slowly. As the fingertip is released, the deformed membrane 103 restores the original condition due to its elastic repulsive force to produce negative pressure in the inside of the device so that the blood exuded from the fingertip is conveyed into the inside of the device by way of the through holes formed by the needling needles 102 to get to the support body 104. The body fluid (blood) sampling operation ends when the body fluid penetrates into the support body 104.

Example 2

Figure 3:
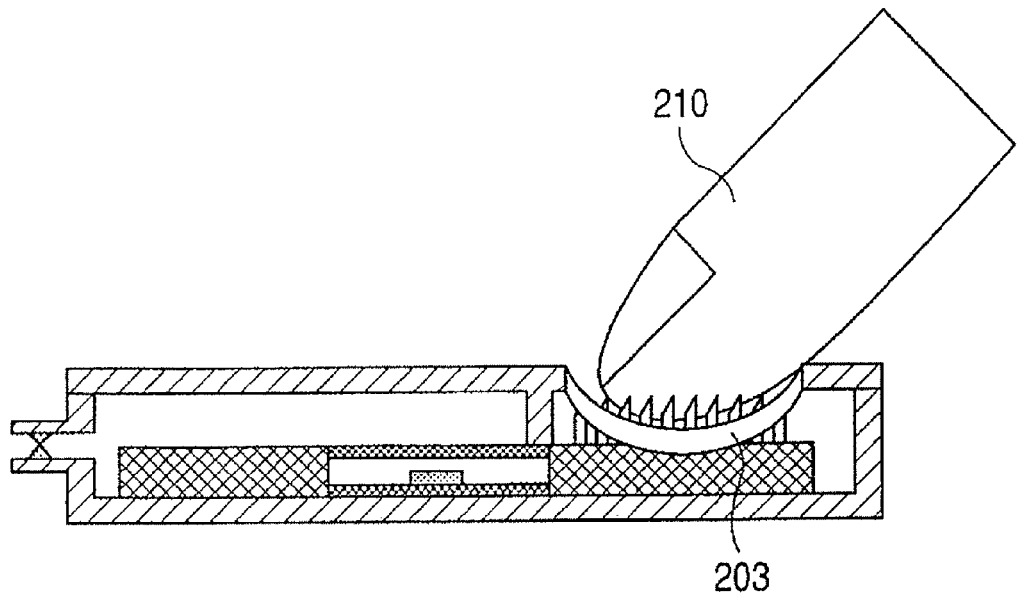
FIG. 3 is a schematic vertical cross sectional view of the analyzing device of Example 2 in operation.
Figure 5:
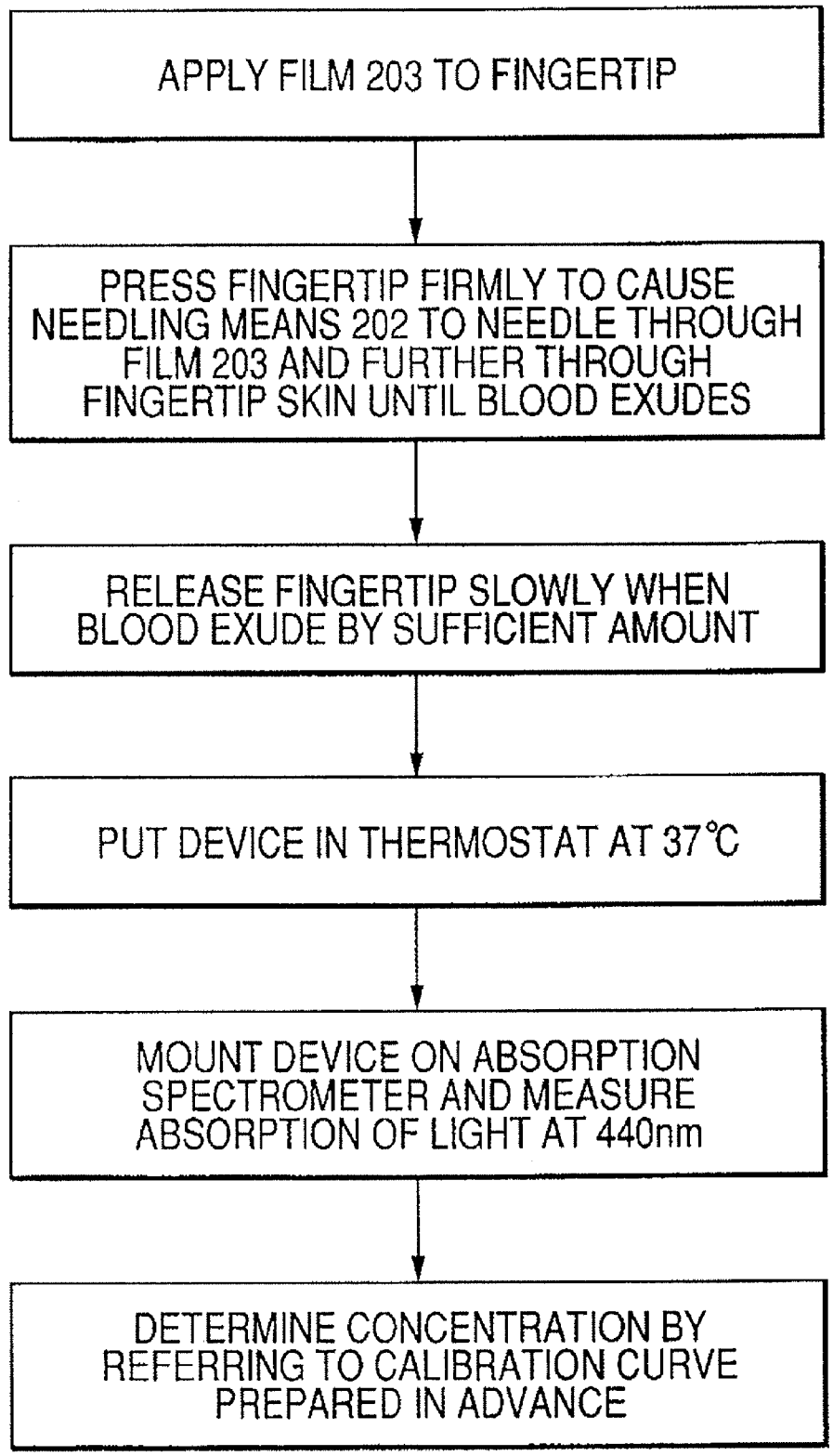
FIG. 5 is a flowchart of the body fluid sampling and analyzing process of Example 2.

An example of analyzing blood by means of a body fluid analyzing device according to the invention will be described below by referring to FIGS. 2A, 2B and FIG. 3 and the flowchart of FIG. 5. In this example, γ-GTP (γ-glutamyl-transpeptidase) that is an enzyme contained in blood and operates as index for the function of the liver is analyzed. The γ-GTP analysis is performed by optically measuring the absorption of light at the wavelength of 440 nm by p-nitroaniline out of the L-glutamylglycilglycine and p-nitroaniline produced by a reaction caused by γ-GTP, using L-γ-glutamyl-p-nitroanilide and glycilglycin as substrate. Thus, the housing 209 used in this example is made of, for example, glass that transmits light including the wavelength to be detected and does not absorb light at and near the wavelength of 400 nm.

Now, the flow of operation from actually sampling blood to analyzing the sample blood will be described. Firstly, as in Example 1, an index finger or middle finger is applied onto the membrane 203 of the body fluid analyzing device as shown in FIG. 2. The bottom of the device may be rigidly secured onto a desk or the like or supported by a thumb. Then, the finger applied onto the membrane 203 is pressed firmly. The extent (displacement) and the time of pressing are such that the needling means (which is needling needles in this case) 202 needles through the membrane 203 and further through the skin of the fingertip to cause a sufficient amount of liquid to be exuded so as to achieve the objective of blood sampling. At this time, air is discharged from the inside of the device to the outside by way of the check valve 205 by a quantity corresponding to the extent of deformation of the membrane 203 produced by the fingertip applied thereto. FIG. 3 schematically illustrates such a situation.

Once a sufficient amount of blood is sampled, the fingertip pressed against the membrane 203 is released slowly. As the fingertip is released, the deformed membrane 203 restores the original condition due to its elastic repulsive force to produce negative pressure in the inside of the device so that the blood exuded from the fingertip is conveyed into the inside of the device by way of the through holes formed by the needling needles 202 to get to the support body 204. Thus, body fluid (blood) is sampled as the body fluid penetrates into the support body 204. Then, the analyzing device is put into a thermostat (not shown) at 37° C. Note that the analyzing device is in a condition where the device can be put into the thermostat by this time.

The blood that penetrated into the support body 204 is filtered to produce blood plasma, which is moved to the liquid transport path 206 due to the capillary phenomenon and eventually gets to the reaction/detection section 207. L-γ-glutamyl-p-nitroanilide and glycilglycin that are the substrate of γ-GTP are borne in the reaction/detection section 207 in advance by an amount remarkably in excess of the amount necessary for the reaction caused by γ-GTP in usual blood. Additionally, the reaction/detection section 207 is so designed that it can hold only a predetermined quantity of blood plasma. After the elapse of a predetermined time period, this device is mounted on an absorption spectrophotometer (not shown), the extent of absorption of light at the wavelength of 440 nm is measured and the concentration is determined by referring to the calibration curve prepared in advance to end the operation of analyzing the γ-GTP in the blood sample. Note that, the thermostat and the absorption spectrophotometer used in the example may be integrated.

According to the embodiment of the present invention, it is possible to provide a body fluid sampling device that satisfies at least the performance requirements (1) and (2) listed above. Then, as a result, it is possible for the subject him- or herself or the person in charge of a hospital or a laboratory to examine the specimen for infectious diseases and the health condition in a simple manner that minimizes the psychological barrier of the subject if the object of examination is body fluid such as blood. Additionally, a body fluid sampling device according to the embodiment of the present invention allows the subject to sample blood from a fingertip by a single hand without requiring the use of a special support body because it is so designed that the sampler can needle the fingertip by him- or herself. More specifically, the subject places the site of sampling on the membrane (103 in FIG. 1) that contains needling needles under it and then applies force for the purpose of needling and sampling. In this way, the subject can reliably sample body fluid at a desired part of the body.

Finally, since a body fluid sampling device according to the embodiment of the present invention is so designed that the subject samples body fluid through the membrane (103 in FIG. 1), the sampled body fluid is exposed to air only for a minimal time period to prevent the sampled body fluid from being degraded by oxygen in air. Thus, consequently, it is possible to accurately examine the sampled body fluid.

This application claims benefit of Japanese Patent Application No. 2006-003658, filed Jan. 11, 2006, which is hereby incorporated by reference herein in its entirety.

What is claimed is:
1. A body fluid sampling device for sampling body fluid from a living body via a body fluid sampling surface, said device comprising:
a housing having a hermetically sealable internal region;
an elastically deformable section arranged at a part of a partition wall separating the internal region from an outside and adapted to be applied to the body fluid sampling surface; and
a needle arranged in the internal region so as to needle the body fluid sampling surface and cause body fluid to exude from the body fluid sampling surface;
wherein the needle is arranged at a position adapted to needle through the elastically deformable section when the elastically deformable section is pressed by the body fluid sampling surface to produce a through hole in the elastically deformable section and further needle through the body fluid sampling surface,
wherein the elastically deformable section has a mechanism for generating negative pressure in the internal region when the elastically deformable section returns to an original position from a pressed position, and
wherein the elastically deformable section is configured to elastically deform towards and press against the needle, thereby causing the needle to needle therethrough, when the elastically deformable section is applied to the body fluid sampling surface.

2. The device according to claim 1, wherein
the elastically deformable section is formed by an elastic membrane, and the device further comprises a check valve arranged in a communication path so that the check valve allows gas to flow only from the internal region to the outside.

3. The device according to claim 2, wherein
The needle is arranged at a position facing the body fluid sampling surface with the membrane interposed between them.

4. The device according to claim 1, further comprising:
detection means for analyzing the contents of the body fluid.

* * * * *